United States Patent [19]

Takei et al.

[11] Patent Number: 5,440,012
[45] Date of Patent: Aug. 8, 1995

[54] CALCITONIN AND METHOD FOR THE PREPARATION AND USE THEREOF

[75] Inventors: Yoshio Takei, Musashino; Akiyoshi Takahashi, Kamaishi; Yuichi Sasayama, Toyama; Masaharu Takigawa, Osaka, all of Japan

[73] Assignee: Sumitomo Metal Industries, Ltd., Osaka, Japan

[21] Appl. No.: 952,735

[22] PCT Filed: May 29, 1992

[86] PCT No.: PCT/JP92/00706

§ 371 Date: Nov. 30, 1992

§ 102(e) Date: Nov. 30, 1992

[87] PCT Pub. No.: WO92/21700

PCT Pub. Date: Oct. 12, 1992

[30] Foreign Application Priority Data

May 31, 1991 [JP] Japan .................................. 3-129695
Sep. 27, 1991 [JP] Japan .................................. 3-249322

[51] Int. Cl.$^6$ ............................................. A61K 38/23
[52] U.S. Cl. ...................................... 530/307; 530/324
[58] Field of Search .................... 530/324, 307; 514/12

[56] References Cited

U.S. PATENT DOCUMENTS 4,397,780 8/1983 Orlowski et al. ................. 260/112.5

FOREIGN PATENT DOCUMENTS 48-98009 12/1973 Japan .

OTHER PUBLICATIONS

"Immunohistochemical Demonstration of Calcitonin Gene-Related Peptide in the Ultimobranchial Gland of Some Lower Vertebrates and in the Nervous Tissues of Some Invertebrates", Yuichi Sasayama et al., *Zoological Science*, vol. 6, pp. 423-426 (1989).

Y. Takei et al, *Biol. Bull,* 180, Jun. 1991, "New Calcitonin Isolated from the Ray, *Dasyatis akajei*," pp. 485–488.

*Primary Examiner*—Jill Warden
*Assistant Examiner*—David Lukton
*Attorney, Agent, or Firm*—Burns, Doane, Swecker & Mathis

[57] ABSTRACT

A calcitonin originated from the ultimobranchial gland of cartilaginous fishes and having a blood calcium-decreasing activity has the following amino acid sequence: H-Cys-Thr-Ser-Leu-Ser-Thr-Cys-Val-Val-Gly-Lys-Leu-Ser-Gln-Gln-Leu-His-Lys-Leu-Gln-Asn-Ile-Gln-Arg-Thr-Asp-Val-Gly-Ala-Ala-Thr-Pro-NH$_2$, where the cysteine residues in the peptide may be linked together through a disulfide bond. The novel peptide exhibits an excellent blood calcium-decreasing activity and an excellent chondrocyte differentiation-promoting activity and is useful as a therapeutic agent for hypercalcemia, osteoporosis, Paget's disease, and the like.

3 Claims, 1 Drawing Sheet

FIG. 1

| | Sequence |
|---|---|
| (This Invention) Stingray Calcitonin | C T S L S T C V V G K L S Q Q L H K L Q N I Q R T D V G A A T P –NH₂ |
| (Prior Art) | |
| Fowl Calcitonin | C A S L S T C V L G K L S Q E L H K L Q T Y P R T D V G A G T P –NH₂ |
| Eel Calcitonin | C S N L S T C V L G K L S Q E L H K L Q T Y P R T D V G A G T P –NH₂ |
| Salmon Calcitonin | C S N L S T C V L G K L S Q E L H K L Q T Y P R T N T G S G T P –NH₂ |
| Rat Calcitonin | C G N L S T C M L G T Y T Q D L N K F H T F P Q T S I G V G A P –NH₂ |
| Human Calcitonin | C G N L S T C M L G T Y T Q D F N K F H T F P Q T A I G V G A P –NH₂ |
| Swine Calcitonin | C S N L S T C V L S A Y W R N L N N F H R F S G M G F G P E T P –NH₂ |
| Bovine Calcitonin | C S N L S T C V L S A Y W K D L N N T H R F S G M G F G P E T P –NH₂ |
| Sheep Calcitonin | C S N L S T C V L S A Y W K D L N N Y H R Y S G M G F G P E T P –NH₂ |

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note="amino acid 1 =H"

( i x ) FEATURE:
        ( A ) NAME/KEY: Peptide
        ( B ) LOCATION: 2..8
        ( D ) OTHER INFORMATION: /note="amino acids 2-8 =disulfide
            bond or ethylene ethylene bond."

( i x ) FEATURE:
        ( A ) NAME/KEY: Peptide
        ( B ) LOCATION: 34
        ( D ) OTHER INFORMATION: /note="amino acid 34 =NH2"

( x i ) SEQUENCE DESCRIPTION: SEQ ID NO:1:

```
Xaa  Cys  Thr  Ser  Leu  Ser  Thr  Cys  Val  Val  Gly  Lys  Leu  Ser  Gln  Gln
 1                    5                        10                        15

Leu  His  Lys  Leu  Gln  Asn  Ile  Gln  Arg  Thr  Asp  Val  Gly  Ala  Ala  Thr
               20                        25                        30

Pro  Xaa
```

( 2 ) INFORMATION FOR SEQ ID NO:2:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

(A) NAME/KEY: Peptide
(B) LOCATION: 1
(D) OTHER INFORMATION: /note="amino acid 1 =X."

(ix) FEATURE:
(A) NAME/KEY: Peptide
(B) LOCATION: 2..8
(D) OTHER INFORMATION: /note="amino acids 2-8 = may be disulfide bond or ethylene-ethylene bond."

(ix) FEATURE:
(A) NAME/KEY: Peptide
(B) LOCATION: 34
(D) OTHER INFORMATION: /note="amino acid 34 =NH2."

(xi) SEQUENCE DESCRIPTION: SEQ ID NO:2:

Xaa Cys Thr Ser Leu Ser Thr Cys Val Val Gly Lys Leu Ser Gln Gln
1               5                   10                  15

Leu His Lys Leu Gln Asn Ile Gln Arg Thr Asp Val Gly Ala Ala Thr
                20                  25                  30

Pro Xaa (2) INFORMATION FOR SEQ ID NO:3:

(i) SEQUENCE CHARACTERISTICS:
(A) LENGTH: 32 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:3:

Cys Thr Ser Leu Ser Thr Cys Val Val Gly Lys Leu Ser Gln Gln Leu
1               5                   10                  15

His Lys Leu Gln Asn Ile Gln Arg Thr Asp Val Gly Ala Ala Thr Pro
                20                  25                  30

(2) INFORMATION FOR SEQ ID NO:4:

(i) SEQUENCE CHARACTERISTICS:
(A) LENGTH: 32 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

Cys Ala Ser Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
                20                  25                  30

(2) INFORMATION FOR SEQ ID NO:5:

(i) SEQUENCE CHARACTERISTICS:
(A) LENGTH: 32 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
                20                  25                  30

( 2 ) INFORMATION FOR SEQ ID NO:6:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Cys Ser Asn Leu Ser Thr Cys Val Leu Gly Lys Leu Ser Gln Glu Leu
1               5                   10                  15
His Lys Leu Gln Thr Tyr Pro Arg Thr Asn Thr Gly Ser Gly Thr Pro
                20                  25                  30
```

( 2 ) INFORMATION FOR SEQ ID NO:7:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Cys Gly Asn Leu Ser Thr Cys Met Leu Gly Thr Tyr Thr Gln Asp Leu
1               5                   10                  15
Asn Lys Phe His Thr Phe Pro Gln Thr Ser Ile Gly Val Gly Ala Pro
                20                  25                  30
```

( 2 ) INFORMATION FOR SEQ ID NO:8:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Cys Gly Asn Leu Ser Thr Cys Met Leu Gly Thr Tyr Thr Gln Asp Phe
1               5                   10                  15
Asn Lys Phe His Thr Phe Pro Gln Thr Ala Ile Gly Val Gly Ala Pro
                20                  25                  30
```

( 2 ) INFORMATION FOR SEQ ID NO:9:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Cys Ser Asn Leu Ser Thr Cys Val Leu Ser Ala Tyr Trp Arg Asn Leu
1               5                   10                  15
Asn Asn Phe His Arg Phe Ser Gly Met Gly Phe Gly Pro Glu Thr Pro
                20                  25                  30
```

( 2 ) INFORMATION FOR SEQ ID NO:10:

( i ) SEQUENCE CHARACTERISTICS:
        ( A ) LENGTH: 32 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:10:

Cys Ser Asn Leu Ser Thr Cys Val Leu Ser Ala Tyr Trp Lys Asp Leu
1               5                   10                  15

Asn Asn Thr His Arg Phe Ser Gly Met Gly Phe Gly Pro Glu Thr Pro
            20                  25                  30

(2) INFORMATION FOR SEQ ID NO:11:

(i) SEQUENCE CHARACTERISTICS:
    (A) LENGTH: 32 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:11:

Cys Ser Asn Leu Ser Thr Cys Val Leu Ser Ala Tyr Trp Lys Asp Leu
1               5                   10                  15

Asn Asn Tyr His Arg Tyr Ser Gly Met Gly Phe Gly Pro Glu Thr Pro
            20                  25                  30

CALCITONIN AND METHOD FOR THE PREPARATION AND USE THEREOF

TECHNICAL FIELD

The present invention relates to a novel peptide and more paticularly to a calcitonin originating from the ultimobranchial glands of cartilaginous fishes. The invention also relates to a method for the preparation of the peptide and a pharmaceutical composition comprising the peptide as an active ingredient which is effective as a blood calcium-decreasing agent and a chondrocyte (cartilage cell) differentiation-promoting agent.

BACKGROUND ART

Calcitonin (abbreviated as CT) is a peptide hormone which participates in metabolism of minerals such as calcium and phosphorus and which is found in the thyroid glands of mammals and the ultimobranchial glands of birds and cartilaginous fishes.

The structures of calcitonins mainly originating from the thyroid glands of mammals have been identified for swine (Potts et al, Pro. Natl. Acad. Sci. USA 59: 1321–1328, 1968), humans (Neher et al, Nature 220: 984–996, 1968), bovines (Brewer et al, Biochemistry 63: 940–947, 1969), sheep (Potts et al, Calcium, Parathyroid Hormone and the Calcitonin: 121–127, 1972), and rats (Raulais et al, Eur. J. Biochem. 64: 607–611, 1976).

The structures of calcitonins mainly originating from the ultimobranchial glands have been identified for salmon (Niall et al, Pro. Natl. Acad. Sci. USA 64: 771–778, 1969), eels (Kotani et al, J. Biochem. 79: 345–352, 1976), and fowl (Homma et al, J. Biochem. 100: 459–467, 1986).

As shown in FIG. 1, the calcitonins which have heretofore been identified can be classified into three lineages: a swine lineage including swine, bovines, and sheep, a human lineage including humans and rats, and a salmon lineage including salmon, eels, and fowl. Each of these calcitonins is a single-chain polypeptide consisting of 32 amino acids in which the first and seventh amino acids are linked through a disulfide bond (S—S bond) to form a seven-membered ring with prolineamide present at the carboxyl terminus.

The above-described calcitonins are known to particiapte in the metabolic regulation of blood serum calcium and the bone metabolism. It has recently been found that, in addition to these activities, calcitonins also have an analgesic activity as a neurotransmitter and an antiulcer activity through calcium metabolism. However, the activities of calcitonins have not been elucidated completely. It is also known that the intensities of physiological activities of calcitonins greatly differ among the above-described lineages, e.g., in such a manner that those calcitonins originating from the ultimobranchial glands are much more potent than those calcitonins originating from the thyroid grands. For example, salmon calcitonin has an activity for decreasing the blood calcium level in humans which is about 30 times as high as that of human calcitonin.

Some calcitonins such as salmon and eel calcitonins or their derivatives have been commercially produced by means of chemical synthesis or genetic engineering, and they are available and used for treatment of osteoporosis and similar diseases. However, it is expected that these prior-art calcitonins lose their activities due to an increase in antibody level caused by long-term administration thereof. Accordingly, for therapeutic use of calcitonins, it is desired to find a novel calcitonin which does not belong to any of the above-described lineages of calcitonins. Such a novel calcitonin will be helpful in investigations to elucidate the physiological activities of calcitonins.

DISCLOSURE OF INVENTION

For the purpose of finding a novel calcitonin of a type which is different from known calcitonins, the inventors of the present invention focused on the ultimobranchial glands of cartilaginous fishes, which have not in the past been excised to isolate calcitonins. As described above, it is expected that a calcitonin originating from the ultimobranchial glands may have a strong physiological activity. As a result of investigations, it has been found that a blood calcium-decreasing factor having a strong activity is present in the ultimobranchial glands of cartilaginous fishes. This active factor is a novel calcitonin peptide which is of a type different from any known calcitonin and it is useful in pharmaceutical compositions since it has a blood calcium-decreasing activity and a chondrocyte differentiation-promoting activity.

The present invention provides a novel peptide originating from the ultimobranchial gland of a cartilaginous fish and having a blood calcium-decreasing activity and a chondrocyte differentiation-promoting activity. The peptide has a molecular weight of 3400±400.

The present invention also relates to a peptide having an amino acid sequence (SEQ. ID NO: 1) of the following formula and its salt.

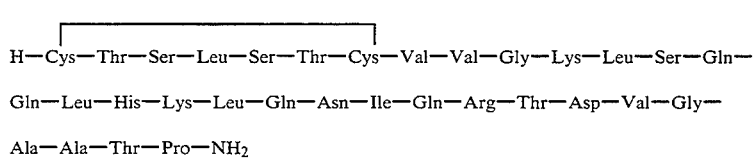

(I)

The two cysteine residues (Cys) in the above amino acid sequence of the peptide are linked together through a disulfide (S—S) bond or an ethylene-ethylene bond. The structure of the peptide is also shown in FIG. 1.

More generally, the present invention relates to a peptide having an amino acid sequence (SEQ. ID NO: 2) of the following formula (II) and its salt.

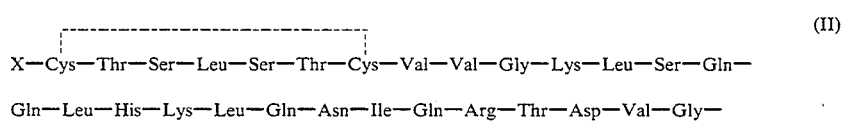

(II)

Ala—Ala—Thr—Pro—NH₂

In the above formula, X is hydrogen, Tyr-, or a radical capable of being labeled with an isotope, and the two cysteine residues in the peptide may be linked together through a disulfide bond or an ethylene-ethylene bond.

The isotope-labelable radical usable as X may be any such a radical which includes, for example, an aromatic radical which can be labeled with $^{125}$I or deuterium.

The present invention also relates to a blood calcium-decreasing agent and a chondrocyte differentiation-promoting agent comprising the above-described peptide or its salt as an active ingredient. Thus, there is a possibility of using the peptide of the present invention in the treatment of hypercalcemia, osteoporosis, osteitis deformans (Paget's disease), dwarfism, bone fracture, and the like. The peptide is also useful as an analgesic in pharmaceutical compositions.

The peptide of the present invention is a calcitonin originating from the ultimobranchial gland of the stingray (Dasyatis akajei), a cartilaginous fish. In vertebrates having a bony skeleton, its calcitonin participates in the inhibition of calcium dissolution from the bone or strengthening of the bone owing to an increase in the concentration of bone-salt in the bone. Cartilaginous fishes are different from other vertebrates in that they have a cartilaginous skeleton, so it is hardly conceivable that the physiological activities of calcitonin in cartilaginous fishes are exactly the same as those in other vertebrates having a bony skeleton and it is expected that calcitonin in cartilaginous fishes have different physiological activities.

The peptide of the present invention is a novel type of calcitonin having a structure which does not belong to any of the known lineages of calcitonins. Therefore, it is expected that the peptide will play a great role in investigations to elucidate the mechanism of metabolic regulation of blood calcium, causes for abnormal bone metabolism diseases, and physiological activities of calcitonins. For example, when X in the above formula (II) is Tyr- or an isotope-labelable radical, the peptide of the present invention can be labeled and the resulting labeled peptide can be used to determine the blood concentration of the peptide or to measure the half-life or affected area, which is, in turn, helpful in the elucidation of metabolic kinetics of the peptide.

Since the calcitonin of the present invention is a novel type of calcitonin, it is expected that, when administered as a therapeutic agent for osteoporosis, for example, the calcitonin will be effective even in those patients on whom the prior-art calcitonins have no significant effect due to antibody production by the immunity in the body of the patients.

The peptide of the present invention can be prepared by isolating and recovering it from those cells in which the peptide is produced. Useful peptide-producing cells include tissue cells of the ultimobranchial gland of the stingray, a cartilaginous fish, or grown cells obtained by cell culture of the tissue cells, and cells obtained by a gene recombination technique and capable of producing the desired calcitonin peptide. The peptide can be isolated from these cells and purified by using a combination of various techniques conventionally employed in isolation and purification of peptides which include extraction, gel-permeation chromatography, ion-exchange chromatography, high-performance liquid chromatography, electrophoresis, and recrystallization. In particular, it is preferred that reversed phase, high-performance liquid chromatography be employed in the isolation and purification of the peptide.

Alternatively, it is also possible to chemically synthesize the peptide from amino acids on the basis of the information on the amino acid sequence which was found by analysis of the isolated and purified calcitonin. The synthesis can be performed using a conventional peptide synthesis method, for example, a solid-phase amino acid synthesis method of Yanagisawa et al, or a liquid-phase amino acid synthesis method.

BRIEF DESCRIPTION OF DRAWING

FIG. 1 shows amino acid sequences (SEQ. ID NOS: 3-11) of known calcitonins along with that of the calcitonin of the present invention.

In the figure, the amino acids are indicated by one-letter abbreviations, which correspond to the following three-letter abbreviations:

| A: Ala | C: Cys | D: Asp | E: Glu | F: Phe | G: Gly |
|--------|--------|--------|--------|--------|--------|
| H: His | I: Ile | K: Lys | L: Leu | M: Met | N: Asn |
| P: Pro | Q: Gln | R: Arg | S: Ser | T: Thr | V: Val |
| W: Trp | Y: Tyr |        |        |        |        |

BEST MODE FOR CARRYING OUT THE INVENTION

The isolation and purification of the calcitonin from the tissue of a stingray will be described below.

At first, the ultimobranchial gland of a stingray is excised. This fish has a pair of ultimobranchial glands on the backside of the heart, and they can be visually identified and easily excised. A desired large amount of the cells can be obtained either by collecting a number of the ultimobranchial glands by excision or by growing the tissue cells of the ultimobranchial gland by cell culture.

After the excised ultimobranchial glands are frozen, they are fragmented and boiled in distilled water. After cooling, acetic acid is added and the mixture is homogenized to perform extraction. The extract is centrifuged and the resulting supernatant is again centrifuged after acetone is added thereto. The supernatant is evaporated to dryness in vacuo and the residue is taken up in acetic acid. The resulting solution is then centrifuged after addition of acetone. The sediment is taken up in a 0.1% trifluoroacetic acid solution and the resulting solution is subjected to reversed phase, high-performance liquid chromatography. The fraction which is found to be active by the immunoblotting method is collected and purified by being subjected again to reversed phase, high-performance liquid chromatography.

The amino acid sequence of the thus-isolated stingray calcitonin can be determined by using an automatic amino acid sequence analyzer in which the peptide bonds are sequentially severed from the N-terminus by the Edman degradation method and the liberated amino acids are identified by high-performance liquid chromatography. The result is shown as SEQ ID No. 1 in the affixed Sequence Listing.

The amino acid analysis of the recovered peptide gave the following amino acid composition:

Asp 2.0 (2), Gln 4.6 (4), CM-Cys 1.3 (2), Ser 3.0 (3), Gly 2.2 (2), His 1.0 (1), Arg 1.1 (1), Thr 4.2 (4), Ala 2.2 (2), Pro 1.1 (1), Val 2.4 (3), Ile 1.0 (1), Leu 4.2 (4), Lys 2.0 (2).

The numbers in parentheses indicate the theoretical molar content of each amino acid.

The naturally-occurring peptide isolated from the ultimobranchial gland of a stingray has a molecular weight of 3395 and a structure represented by the foregoing formula (I) in which the two cysteine residues are linked together through a disulfide bond.

On the basis of these results, the stingray calcitonin represented by formula (I) can be synthesized by preparing a straight-chain peptide having the amino acid sequence shown as SEQ ID No. 1, for example, in accordance with Yanagisawa's method (Pro. Natl. Acad. Sci. USA 85: 6964–6967, 1988) and linking the two cysteine residues through a disulfide bond or an ethylene-ethylene bond and modifying the C-terminus to form an amide by using suitable known reactions. If necessary, a peptide represented by the foregoing formula (II) can be synthesized by introducing a tyrosine residue or an isotope-labelable radical at the N-terminus of the resulting calcitonin by a known reaction and by performing or omitting the reaction for linking between the two cysteine residues.

The physiological activities of the pure naturally-occurring stingray calcitonin extracted from the ultimobranchial gland of a stingray and those of synthetic stingray calcitonin obtained in the above-described manner were determined according to the technique of Homma et al (J. Biochem. 100: 459–467, 1986). It was found that both have a strong blood calcium-decreasing activity.

When their physiological activities on cartilage cells or chondrocytes were determined according to the technique of Bessey et al (J. Biol. Chem. 164: 321–329, 1964) and that of Lowry et al (J. Biol. Chem. 193: 265–275, 1951), a strong cell differentiation-promoting activity was noted.

The peptide of the present invention which has a structure given by the foregoing formula (I) and which can be isolated from the ultimobranchial glands of cartilaginous fishes has a significant activity of decreasing the blood calcium level which is comparable to the activities of conventionally-used salmon and eel calcitonins. Therefore, it can be used as a therapeutic agent for osteoporosis, hypercalcemia, and Paget's disease. It also has an activity as a nerve peptide and hence can be used as an analgesic. Since the peptide originates from cartilage fishes, it exhibits an excellent activity of promoting chondrocyte differentiation and is useful as a therapeutic agent for dwarfism, bone fracture, and osteoporosis. The peptide is particularly advantageous in that it is effective for those patients on whom conventional calcitonins have no effect.

In addition to clinical use in therapy, the peptide of the present invention can be used in investigations to elucidate the biological mechanisms of calcium regulation and bone metabolism. For these purposes, a wider range of peptides represented by formula (II) are useful. Namely, in such cases, the cysteine residues may not be linked together and it is preferred that Tyr- or an isotope-labelable radical be attached to the N-terminus.

When administered as a therapeutic agent, the peptide of the present invention can be administered orally or parenterally, e.g., by intravenous, intramuscular, or subcutaneous injection, or topically, e.g., in the form of eye drops or nasals, although intramuscular injection is particularly preferred for the peptide.

The dose is in the range of 0.01–100 nmol/kg. In the case of intramuscular injection, a dose of the peptide which is selected depending on the body weight and the expected effect is applied usually in the form of a solution dissolved in 0.1 to 10 ml of physiological saline.

When the peptide is used as an active ingredient in a pharmaceutical composition, the peptide and one or more additives may be formulated into various forms including emulsions, waters, solutions, tablets, powders, granules, capsules, pills, and the like.

Additives which can be used in the formulation include pharmacologically acceptable isotonic agents, stabilizers, preservatives, pH adjusting agents, excipients, disintegrants, lubricants, binders, dispersing agents, plasticizers, and the like. For example, sodium chloride can be used as an isotonic agent, purified gelatine as a stabilizer, phenol as a preservative, hydrochloric acid and sodium hydroxide as pH adjusting agents, lactose and glucose as excipients, starch and agar as disintegrants, talc and liquid paraffin as lubricants, single syrup and ethanol as binders, methylcellulose and ethylcellulose as dispersing agents, and glycerol and starch as plasticizers.

EXAMPLE 1

Isolation and Purification of Stingray Tissue

A 2.2 g amount of the ultimobranchial glands collected from the bodies of 200 stingrays by excision were frozen at $-50°$ C. and then fragmented in a mincer. To the fragments, 7 volumes of distilled water were added and boiled for 5 minutes. Upon cooling, acetic acid was added to give a concentration of 1M and homogenized in a Polytron mixer. The resulting suspension was centrifuged at $4°$ C. and $25,000 \times G$ for 30 minutes. To the supernatant, 2 volumes of cold acetone were added so as to give an acetone concentration of 67% and centrifuged at $4°$ C. and $16,000 \times G$ for 30 minutes. The supernatant was distilled in vacuo to remove acetone and the residue was lyophilized. The resulting powder was dissolved in 10 ml of 1M acetic acid solution, and 600 ml of cold acetone was added to give an acetone concentration of 98.5%. The solution was centrifuged at $16,000 \times G$ for 30 minutes.

The collected sediment was dried and then dissolved in an aqueous 0.1% trifluoroacetic acid solution, and the resulting solution was subjected to reversed phase, high-performance liquid chromatography under the following conditions.

Conditions 1:
Column: $4.6 \times 250$ mm column (Toso, ODS-120T),
Flow rate: 1 ml/min,
Eluent:
  A = a mixture of an aqueous 0.1% trifluoroacetic acid solution and acetonitrile (8:2)
  B = a mixture of an aqueous 0.1% trifluoroacetic acid solution and acetonitrile (2:8)
Elution: linear concentration-gradient elution from Eluent A to Eluent B (60 minutes).

Each of the collected fractions was examined by the immunoblotting method using the fact that antisalmon calcitonin serum is cross-reactive with the calcitonin of the present invention to obtain an active fraction (No. 12) in the following manner. Each fraction which had been lyophilized and synthetic salmon calcitonin were dissolved in 10 μl of a mixture of a 0.1M sodium carbonate solution and methanol [4:1 (V/V), pH 9.5] and the resulting solution was dropped onto a nylon membrane (Millipore, Immobilin PVDF Transfer Membrane) and adsorbed by the membrane. After the membrane was dipped in 100% methanol for 3 seconds, it was washed three times with a 10 mM phosphate buffer (pH 7.2, abbreviated as PBST) containing 0.05% Tween 20, subsequently washed two times with PBST containing 1% goat serum, and finally washed three times with PBST. The washed membrane was reacted for 2 hours at room temperature with antiserum (diluted to 1/4000) collected from a rabbit which had been immunized against synthetic salmon calcitonin. After washing three times with PBST, the membrane was subjected to immune staining using a Vectastain ABC kit (Vector Laboratories) to identify an active fraction.

The active fraction which had been lyophilized was subjected again to reversed phase, high-performance liquid chromatography in the same manner as described above under the following conditions.

Conditions 2:
Column: 4.6×250 mm column (Toso, ODS-120T),
Flow rate: 1 ml/min,
Eluent:
  A = a mixture of water, acetonitrile, and 1M ammonium acetate (pH 4.6) (72:8:1, V/V),
  B = a mixture of water, acetonitrile, and 1M ammonium acetate (pH 4.6) (25:100:1, V/V).
Elution: linear concentration-gradient elution from Eluent A to Eluent B (40 minutes)

As a result, a single peak having a strong absorbance (A230) based on a peptide was noted in a certain fraction. The fraction was lyophilized to give 122 nmole of pure stingray calcitonin according to the present invention.

The thus-isolated pure stingray calcitonin (12.2 nmole) was subjected to S-carboxymethylation to sever the S—S bond and the reaction product was purified by reversed phase, high-performance liquid chromatography in the same manner as for Conditions 1. A sample of the purified product was subjected to amino acid analysis and the above-described amino acid composition was determined. Furthermore, another sample of the purified product was subjected to Edman degradation in a conventional manner and the amino acid sequence of the peptide was determined sequentially from the amino terminus by a known amino acid analysis technique. The presence of the proline at the carboxyl terminus in the form of an amide was confirmed by the fact that a single peak was obtained when a sample of the purified product was subjected to high-performance liquid chromatography along with a sample of the amidated synthetic stingray calcitonin obtained in Example 2 under the above-described Conditions 1 and 2. Thus, it was determined that the isolated stingray calcitonin had the amino acid sequence shown as SEQ ID No. 1 in the affixed Sequence Listing. Namely, the calcitonin has the structure of the foregoing formula (I) in which the two cysteine residues are linked through a disulfide bond.

EXAMPLE 2

A peptide consisting of 32 amino acids and having the same amino acid sequence as the stingray calcitonin of the present invention obtained in Example 1 was chemically synthesized according to the method of Yanagisawa et al (Pro. Natl. Acad. Sci. USA 85: 6964–6967, 1988). Using a fully automatic peptide synthesizer (Applied Biosystem), amino acids were coupled by the t-butoxycarbonyl (BOC) method. A disulfide bond was formed between the two cysteine residues in the resulting straight-chain peptide by oxidation of the protecting groups attached to these cysteine residues with potassium ferricyanide. The synthesized product was purified by reversed phase, high-performance liquid chromatography (Shimadzu LC8A).

The synthetic peptide obtained as above was subjected to reversed phase, high-performance liquid chromatography together with the calcitonin obtained in Example 1 and it was confirmed that both peptides had an elution band in the same position.

EXAMPLE 3

Male Wistar rats weighing 90–110 grams (10 animals in each group) which had fasted for 24 hours prior to the experiment were intravenously injected with a standard solution of salmon calcitonin or eel calcitonin or a solution of the synthetic stingray calcitonin (produced in Example 2) each dissolved in an aqueous 0.9% sodium chloride solution (pH 4.6) containing 0.1% bovine serum albumin at a dose of 1 pmol or 10 pmol per animal. Exactly one hour after the administration, a blood sample was collected from the artery of each test animal and the concentration of calcium in the serum was determined by atomic absorption spectroscopy. Based on the values for serum calcium concentration in rats of the groups in which one of the standard solutions was administered at a dose of 1 pmol or 10 pmol per animal and those in rats of the group in which the stingray calcitonin of the present invention was administered at the same dose, the relative titer of the stingray calcitonin was determined by the standard statistical procedures for parallel line assays.

The titers of salmon calcitonin and eel calcitonin used as standard substances were about 3500 IU/mg and about 4500 IU/mg, respectively. On the other hand, the calcitonin of the present invention had a titer of about 3770 IU/mg. Thus, the peptide according to the present invention exhibited an excellent blood calcium-decreasing activity comparable to known calcitonins originating from the ultimobranchial glands.

EXAMPLE 4

A grown cartilage cell culture of rabbit costal cartilage prepared in accordance with the method of Suzuki et al [Yamane and Endo ed., Saishin Soshiki Baiyo Oyo Kenkyu-ho (Modern Tissue Culture Applied Research Methods), 116–128, published by Soft Science, Tokyo, 1985] was suspended in αMEM medium (Flow Laboratory) containing 10% fetal bovine serum in an amount of $3.5 \times 10^4$ cells per milliliter, and 1 ml of the resulting suspension was seeded in each well of a 24-well Multi-Well plate (16 mm in diameter, Corning) which was coated with collagen. The plate was incubated for 9 days at 37° C. in an atmosphere consisting of 5% carbon dioxide and 95% air using a carbon dioxide incubator (Sanyo/Farma). In the course of the incubation, the medium was renewed on the fourth and sixth days and at that time 10 μl of a phosphate buffer solution containing 0.2% bovine serum albumin and $10^{-12}$ mol/ml of a standard calcitonin which was either salmon calcitonin or eel calcitonin or stingray calcitonin of the present invention (synthetic product obtained in Example 2) was added to the medium. As a control, the same buffer solution which contained 0.2% bovine serum albumin but did not contain calcitonin was used.

After incubation for 9 days, the cell layer (1) was recovered and the alkaline phosphatase activity in each well was determined by the method of Bessey et al (J. Biol. Chem. 164: 321–329, 1946) using p-nitrophenylphosphoric acid as a substrate.

The amount of protein in each well was also determined by assaying the recovered cell layer (1) in accordance with the method of Lowry et al (J. Biol. Chem. 193: 265–275, 1951) using bovine serum albumin as a standard substance.

The value for alkaline phosphatase activity per unit weight of protein was calculated from the values for alkaline phosphatase activity and amount of protein determined as above. The calculated value of the control was about 88,150 nmol/30 min/mg-protein. The values of the salmon calcitonin and eel calcitonin standard substances were about 95,000 nmol/30 min/mg-protein and about 103,000 nmol/30 min/mg-protein, respectively. The calcitonin of the present invention had a value of about 106,000 nmol/30 min/mg-protein. Thus, the calcitonin of the present invention exhibited an excellent activity of promoting chondrocyte differentiation.

Industrial Applicability

The present invention provides a novel calcitonin which occurs in the ultimobranchial glands of cartilaginous fishes and which is different from any known lineage of calcitonins. The peptide has an excellent blood calcium-decreasing activity and an excellent chondrocyte differentiation-promoting activity and is useful in pharmaceutical applications as a therapeutic agent for hypercalcemia, osteoporosis, Paget's disease, dwarfism, bone fracture, and the like and as an analgesic. The peptide is expected to play a great role in investigations to elucidate the mechanisms of blood calcium regulation and bone metabolism. Since the structure of the peptide is different from those of eel calcitonin and salmon calcitonin, which have been clinically applied, there is a good possibility that it can be administered to those patients on whom conventional calcitonins have no effect due to antibody production by immunity in the bodies of the patients.

We claim:

1. A peptide having blood calcium-decreasing activity which has the amino acid sequence represented by the following formula:

```
  ┌─────────────────────────────┐
H—Cys—Thr—Ser—Leu—Ser—Thr—Cys—Val—Val—
                      —Gly—Lys—Leu—Ser—Gln—
Gln—Leu—His—Lys—Leu—Gln—Asn—Ile—Gln—Arg—
                      —Thr—Asp—Val—Gly—
          Ala—Ala—Thr—Pro—NH₂,
``` where the to cysteine residues (Cys) in the peptide are covalently bound through a disulfide (S—S) bond or an ethylene-ethylene bond, and a salt thereof.

2. A peptide having the amino acid sequence represented by the following formula:

```
  ┌─────────────────────────────┐
X—Cys—Thr—Ser—Leu—Ser—Thr—Cys—Val—Val—
                      —Gly—Lys—Leu—Ser—Gln—
Gln—Leu—His—Lys—Leu—Gln—Asn—Ile—Gln—Arg—
                      —Thr—Asp—Val—Gly—
          Ala—Ala—Thr—Pro—NH₂
``` where X is hydrogen, or Tyr-, and wherein the two cysteine residues in the peptide are covalently bound through a disulfide bond or an ethylene-ethylene bond or are not covalently bound.

3. A pharmaceutical composition comprising the peptide according to claim 1 or 2 or its salt as an active ingredient and one or more pharmaceutically acceptable additives.

* * * * *